(12) United States Patent
Martinez et al.

(10) Patent No.: US 11,986,296 B2
(45) Date of Patent: May 21, 2024

(54) OMNIPHOBIC PAPER-BASED SMART BANDAGE DEVICES

(71) Applicant: Purdue Research Foundation, West Lafayette, IN (US)

(72) Inventors: Ramses Valentin Martinez, West Lafayette, IN (US); Aniket Pal, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 150 days.

(21) Appl. No.: 16/812,438

(22) Filed: Mar. 9, 2020

(65) Prior Publication Data

US 2020/0297255 A1    Sep. 24, 2020

Related U.S. Application Data

(60) Provisional application No. 62/819,708, filed on Mar. 18, 2019.

(51) Int. Cl.
*A61B 5/1477* (2006.01)
*A61B 5/00* (2006.01)
(Continued)

(52) U.S. Cl.
CPC .......... *A61B 5/1477* (2013.01); *A61B 5/0022* (2013.01); *A61B 5/0531* (2013.01);
(Continued)

(58) Field of Classification Search
CPC . A61B 5/0022; A61B 5/0531; A61B 5/14539; A61B 5/14546; A61B 5/4266; A61B 5/447; A61B 5/6802; A61B 5/14517; A61B 2562/0215; A61B 2560/045; A61B 5/1486; A61B 5/445; A61B 5/1447; A61B 5/6833; A61F 13/00051
See application file for complete search history.

(56) References Cited

U.S. PATENT DOCUMENTS 5,879,292 A     3/1999  Sternberg
2007/0240983 A1*  10/2007  Hsiung ................. G01N 27/26
                                                   204/400
(Continued)

OTHER PUBLICATIONS

Aniket Pal, Debkalpa Goswami et al., Early detection and monitoring of chronic wounds using low-cost, omniphobic paper-based smart bandages, Biosensors and Bioelectronics, vol. 117, 2018, pp. 696-705, ISSN 0956-5663, https://doi.org/10.1016/j.bios.2018.06.060. (Year: 2018).*

(Continued)

*Primary Examiner* — Yi-Shan Yang
*Assistant Examiner* — Kyle W. Kretzer
(74) *Attorney, Agent, or Firm* — Purdue Research Foundation

(57) ABSTRACT

The present disclosure discloses a novel omniphobic, paper-based, smart bandage (OPSB) devices, and the methods to make and use the omniphobic, paper-based, smart bandage devices. The OPSB device of the present disclosure provides a simple, low-cost, and non-invasive strategy to monitor open wound status wirelessly. This disclosure also provides the demonstration of in-vivo early detection and monitoring of pressure ulcers using wireless smart bandages.

3 Claims, 9 Drawing Sheets

(51) Int. Cl.
A61B 5/0531 (2021.01)
A61B 5/145 (2006.01)
(52) U.S. Cl.
CPC ...... *A61B 5/14539* (2013.01); *A61B 5/14546* (2013.01); *A61B 5/4266* (2013.01); *A61B 5/447* (2013.01); *A61B 5/6802* (2013.01); *A61B 5/14517* (2013.01); *A61B 5/6833* (2013.01); *A61B 2562/0215* (2017.08)

(56) References Cited

U.S. PATENT DOCUMENTS

| | | | | |
|---|---|---|---|---|
| 2015/0209198 A1* | 7/2015 | Aizenberg | ........... | C09D 5/1693 428/137 |
| 2017/0156658 A1* | 6/2017 | Maharbiz | ............... | A61B 5/053 |
| 2017/0247739 A1 | 8/2017 | Goluch et al. | | |
| 2017/0325724 A1* | 11/2017 | Wang | .................. | A61B 5/1486 |
| 2018/0055359 A1* | 3/2018 | Shamim | ............... | A61B 5/0004 |
| 2018/0127594 A1* | 5/2018 | Aizenberg | ............. | B65D 25/14 |
| 2018/0267012 A1 | 9/2018 | Scherer | | |
| 2020/0100711 A1* | 4/2020 | Choudhury | .......... | A61B 5/6833 |
| 2020/0305746 A1* | 10/2020 | Futashima | ............... | A61B 5/25 |

OTHER PUBLICATIONS

Pal, Aniket & Cuellar, Hugo & Kuang, Randy & Caurin, Heloisa & Goswami, Debkalpa & Martínez, Ramsés. (2017). Self-Powered, Paper-Based Electrochemical Devices for Sensitive Point-of-Care Testing. Advanced Materials Technologies. 2. 1700130. 10.1002/admt.201700130. (Year: 2017).*

Moiz, Syed Abdul & Imran, S. & Kim, Sang & Nahhas, Professor & Kim, Hee Taik. (2012). Effect of Isopropyl Alcohol for Bimodal dispersion of silver nanoparticles inside polyaniline emeraldine base thin film. Optoelectronics and Advanced Materials-Rapid Communications. 6. 1113-1117. (Year: 2012).*

Glavan, Ana & Martínez, Ramsés & Maxwell, E & Subramaniam, Anand & Nunes, Rui & Soh, Siowling & Whitesides, George. (2013). Rapid fabrication of pressure-driven open-channel microfluidic devices in omniphobic RF paper. Lab on a chip. 13. 10.1039/c3lc50371b. (Year: 2013).*

M. Ochoa, R. Rahimi and B. Ziaie, "Flexible Sensors for Chronic Wound Management," in IEEE Reviews in Biomedical Engineering, vol. 7, pp. 73-86, 2014, doi: 10.1109/RBME.2013.2295817. (Year: 2013).*

Hamedi, M., et al., Electrically Activated Paper Actuators. Adv. Funct. Mater. 2016, 26, 2446-2453.

* cited by examiner

OMNIPHOBIC PAPER-BASED SMART BANDAGE DEVICES

CROSS-REFERENCE TO RELATED APPLICATION

This application claims the priority to U.S. provisional patent Application No. 62/819,708, which was filed Mar. 18, 2019, and the content of which is hereby incorporated by reference in its entirety.

TECHNICAL FIELD

The present disclosure relates to a novel omniphobic, paper-based, smart bandage (OPSB) devices, and the methods to make and use the omniphobic, paper-based, smart bandage devices.

BACKGROUND

This section introduces aspects that may help facilitate a better understanding of the disclosure. Accordingly, these statements are to be read in this light and are not to be understood as admissions about what is or is not prior art.

Chronic wounds, where full regeneration of the damaged tissue does not complete in three months, are a worldwide health problem that causes a significant burden to healthcare systems; both in terms of the number of patients affected and the expenses derived from their prevention and treatment. The need to reduce the burden of chronic wounds on patient's quality of life and national health budgets has led to the development of advanced wound care technologies for automatic monitoring of wound status. These "smart bandages" monitor wound biomarkers using sensors fabricated on flexible substrates in order to reduce the number of dressing changes and minimize the stress and pain suffered by the patient. Effective smart bandages should be mechanically flexible, breathable, easy to apply, and capable of reporting quantitative information about the wound status in real time to guide treatment decisions. Although a variety of smart bandages have been proposed to monitor physical and chemical parameters important in wound healing, most of these devices often require expensive and relatively cumbersome equipment, which limits the mobility of the patients and makes the dressings uncomfortable to wear. Moreover, the need of trained personnel to apply the smart dressings and to interpret the results limits the implementation of these devices outside clinical settings. Since it is recommended to change dressings frequently, smart bandages need to be low cost and disposable for single-use applications.

Therefore, there is a need for lower cost strategy to fabricate sensitive and easy to use smart bandages such that they may be used as single use devices by minimally trained individuals, and may be desirable to improve chronic wound healing outcomes, particularly in resource limited and home environments.

SUMMARY

The present invention provides novel omniphobic paper-based smart bandage devices, and methods to make and use the omniphobic paper-based smart bandage devices.

In one embodiment, the present disclosure provides a device comprising:

a bandage comprising a first surface configured to face a healthy skin or a wounded tissue, and a second surface on the opposite side of the first surface;

a detachable potentiostat, wherein the detachable potentiostat is configured to be attached to the second surface of the bandage;

a porous omniphobic pad comprising a first side configured to be attached to the first surface of the bandage, and a second side that is on the opposite side of the first side; and a sensor deposed on the second side of the porous omniphobic pad, wherein the sensor comprises a working electrode, a counter electrode, and a reference electrode, wherein the detachable potentiostat is configured to be connected to the sensor through a plurality of pathways on the bandage to enable the communications between the potentiostat and the sensor.

In another embodiment, the present disclosure provides a method of detecting a wound condition by attaching the device to a wounded skin area of a patient and monitoring the condition changes with a mobile device.

DETAILED DESCRIPTION

Figure 1:
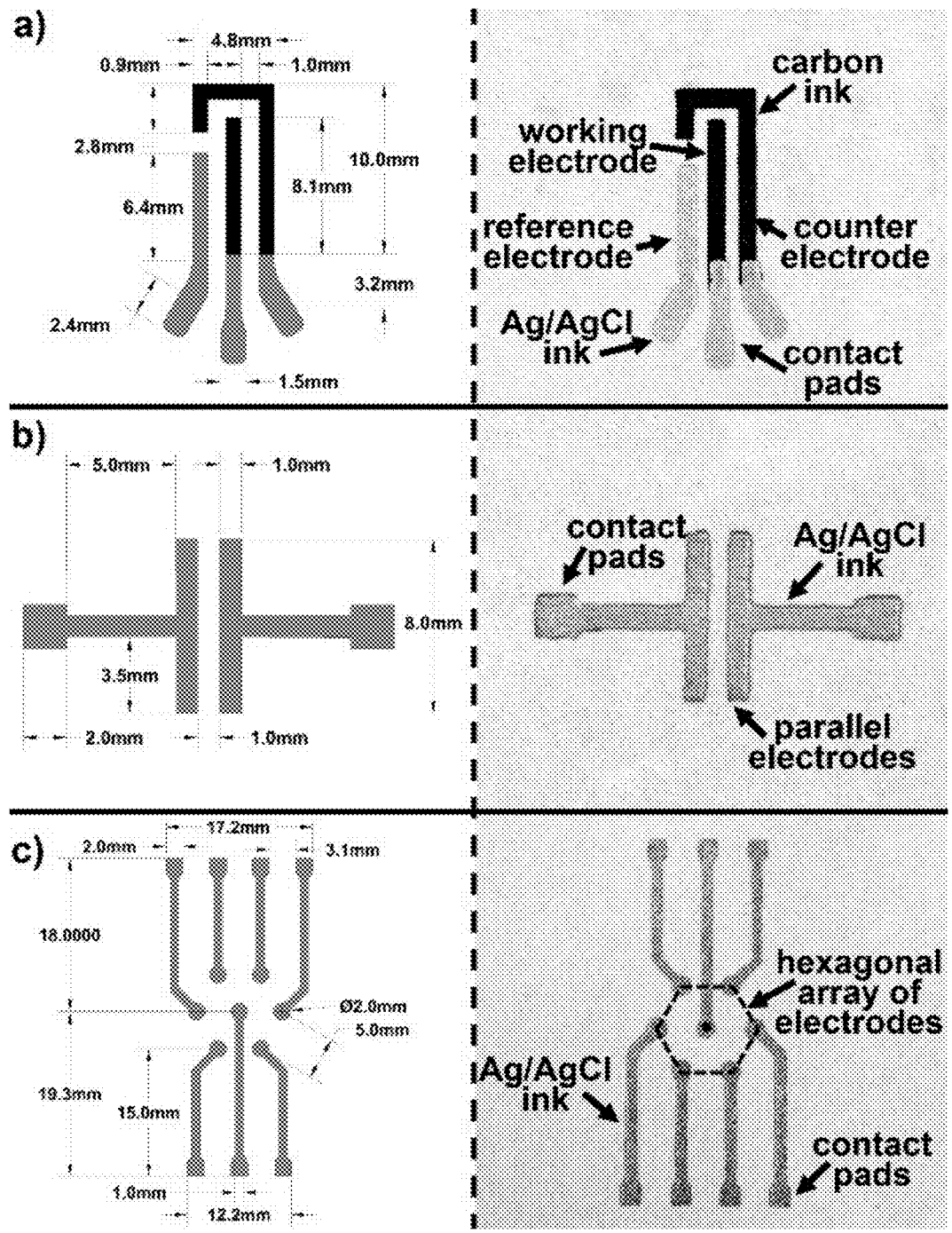
FIG. 1: Schematics and pictures of the stencil-printed electrodes embedded in the OPSB s. (a) Carbon and Ag/AgCl electrodes used for the electrochemical quantification of UA at the wound site. (b) Electrodes used to monitor pH levels at the wound site. (c) Electrode array used for the early detection and monitoring of pressure ulcers on an in-vivo mouse model.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "omniphobic" refers to certain characteristics of a material that is both hydrophobic and oleophobic and capable of repelling various types of liquids such as water, oil, and as well as other contaminants. In one aspect of this disclosure regarding an omniphobic paper, the omniphobic paper is fabricated by applying certain fluorinated alkyltrichlorosilane to a paper substrate. In one aspect, the fluorinated alkyltrichlorosilane may be but is not limited to $CF_3(CF_2)_5(CH)_2SiCl_3$ or trichloro-(1H,1H, 2H,2H-perfluorooctyl)silane.

In one embodiment, the present disclosure provides a device comprising:
  a bandage comprising a first surface configured to face a healthy skin or a wounded tissue, and a second surface on the opposite side of the first surface;
  a detachable potentiostat, wherein the detachable potentiostat is configured to be attached to the second surface of the bandage;
  a porous omniphobic pad comprising a first side configured to be attached to the first surface of the bandage, and a second side that is on the opposite side of the first side; and
  a sensor deposed on the second side of the porous omniphobic pad, wherein the sensor comprises a working electrode, a counter electrode, and a reference electrode,
  wherein the detachable potentiostat is configured to be connected to the sensor through a plurality of pathways on the bandage to enable the communications between the potentiostat and the sensor.

In one embodiment of the present disclosure regarding the device, wherein the device further comprises an absorbent pad deposed on the second side of the porous omniphobic pad.

In one embodiment of the present disclosure regarding the device, wherein the electrodes of the sensor may be but is not limited to printable electrodes, sprayed electrode, laminated electrodes, or sewed electrodes, or any combination thereof.

In one embodiment of the present disclosure regarding the device, wherein one or more chemical materials are provided between one or more electrodes to facilitate the sensing of wound-exudate/sweat/tissue/analytes/signals generated by the tissue under the bandage.

In one embodiment of the present disclosure regarding the device, wherein the sensor may be but is not limited to be configured to detect pH, bacterial infections, the onset of pressure ulcers, uric acid, subcutaneous tissue impedance or any combination thereof.

In one embodiment of the present disclosure regarding the device, wherein the porous omniphobic pad is porous omniphobic paper.

In one embodiment of the present disclosure regarding the device, wherein the electrodes are made of metals, metallic alloys, conductive polymers, organic conductors, conductive ceramic, nanoparticles, liquid metals, conductive textiles, conductive foams, conductive inks, or any combination thereof. In one aspect, the electrodes are made of Ag/AgCl ink, carbon ink, or a combination thereof. In one aspect, Ag/AgCl ink may be used for the reference electrode (RE). In one aspect, the carbon ink may be used for the working electrode (WE) and/or counter electrode.

In one embodiment of the present disclosure regarding the device, wherein the detachable potentiostat is wearable, rechargeable and/or reusable.

In one embodiment of the present disclosure regarding the device, wherein chemical polyaniline emeraldine base and silver micro flakes are provided between one or more electrodes for pH measurement.

In one embodiment of the present disclosure regarding the device, wherein uricase and potassium ferricyanide are provided between one or more electrodes for uric acid measurement.

In one embodiment of the present disclosure regarding the device, wherein one or more electrodes are selectively coated with a conductive hydrogel to minimize the electrical impedance between the skin and the electrodes.

In one embodiment of the present disclosure regarding the device, wherein the printable electrodes are stencil printed.

In one embodiment of the present disclosure regarding the device, wherein the potentiostat is a wireless, reusable, or wearable.

In one embodiment of the present disclosure regarding the device, wherein the potentiostat comprises a rechargeable battery, a microcontroller, a radio frequency communication module, a chip performing electrochemical measurements, and a chip performing impedance spectroscopy.

In one embodiment, the present disclosure provides a method of detecting a wound condition by attaching any device of the present disclosure to a wounded skin area of a patient and monitoring the condition changes with a monitoring device. In one aspect, the monitoring device is a mobile device that may be but is not limited to a mobile phone or a mobile watch.

In one embodiment of the present disclosure regarding the method of detecting a wound condition, wherein the condition to be monitored comprises bacterial infections in open wounds, the onset of pressure ulcers, subcutaneous tissue impedance, pH, pressure ulcer, uric acid, or any combination thereof.

Materials and Methods
Chemicals and Instruments

Whatman #1 paper was obtained from GE Healthcare Inc. Two conductive inks, Ag/AgCl (AGCL-675) and carbon (C-200), was obtained from Applied Ink Solutions. Potassium ferricyanide, potassium ferrocyanide, uric acid, uricase (from *Candida* sp., 4.1 U/mg), polyaniline emeraldine base (PANi-EB, Mw=50 kDa), disodium phosphate (sodium hydrogen phosphate), citric acid (2-hydroxypropane-1,2,3-tricarboxylic acid), and $R^FSiCl_3$ ($CF_3(CF_2)_5(CH_2)_2SiCl_3$, trichloro-(1H,1H,2H,2H-perfluorooctyl)silane) were obtained from Sigma Aldrich Inc. A commercial, benchtop potentiostat (Reference 3000; Gamry Instruments, Warminster, PA) was used to test the performance of the electrochemical sensor and the wearable potentiostat. BAND-AID® adhesive bandages were obtained from Johnson & Johnson Consumer Incorporated Company.

Fabrication of the Wearable Potentiostat

A rechargeable, wearable potentiostat was fabricated by using a low-power programmable front end for electrochemical sensing applications (LMP91000, Texas Inst. Inc.) and a high precision impedance analyzer (AD5933, Analog Devices Inc). The wearable potentiostat is powered by a rechargeable battery (LIR2032, Duracell Inc.), and controlled by an open-source microcontroller prototyping platform (Arduino Nano v3.0, Arduino Inc.) (code is provided at the end of the Specification). An RF transceiver IC (nRF24L01, Nordic Semiconductors Inc.) inside the wearable potentiostat performs for wireless communication through the 2.4 GHz ISM band. The wearable potentiostat was sterilized by spraying 70% ethanol before attaching it to a new omniphobic paper-based smart bandages (OPSB). After the ethanol dried, a laser cut ring of double-sided adhesive tape (410M, 3M Inc.) was used to attach the wearable potentiostat to the bandage and provide a stable electrical connection with the paper-based sensors embedded in the OPSB.

Diffusion Controlled Electrochemical Reactions Governed by the Cottrell Equation During chronoamperometry measurements, a constant voltage (300 mV) was applied and the resulting current due cause by redox reactions between the electrochemical species was measured. Diffusion controlled reactions follow the Cottrell Equation (Eq. S1), where the current i is proportional to the initial concentration Co of the analyte:

$$i = \frac{nFAC^0\sqrt{D}}{\sqrt{\pi t}} \tag{S1}$$

Here n is the number of electrons, F is the Faraday constant (96,485 C/mol), A is the area of the electrode, t is time, and D is the diffusion coefficient. Using the Cottrell equation, the concentration of the analyte can be calibrated by measuring the current of the diffusion controlled electrochemical reaction. Integrating the measured current with respect to time, the net charge exchanged (Q) during the redox reaction was obtained, which also is proportional to the initial concentration. (Eq. S2)

$$Q = \int_0^t i\,dt; \; Q = -\frac{nFAC^0\sqrt{Dt}}{2\sqrt{\pi}} \tag{S2}$$

The value Q was used to calculate the concentration of UA using chronocoulometry.

Oxidation of Uric Acid in OPSBs

Uricase was used in the OPSBs, so that it oxidises UA and produces allantoin (Eq. S3). Potassium ferricyanide is reduced to potassium ferrocyanide to complete the redox couple.

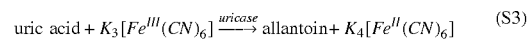

$$\text{uric acid} + K_3[Fe^{III}(CN)_6] \xrightarrow{uricase} \text{allantoin} + K_4[Fe^{II}(CN)_6] \tag{S3}$$

Figure 2:
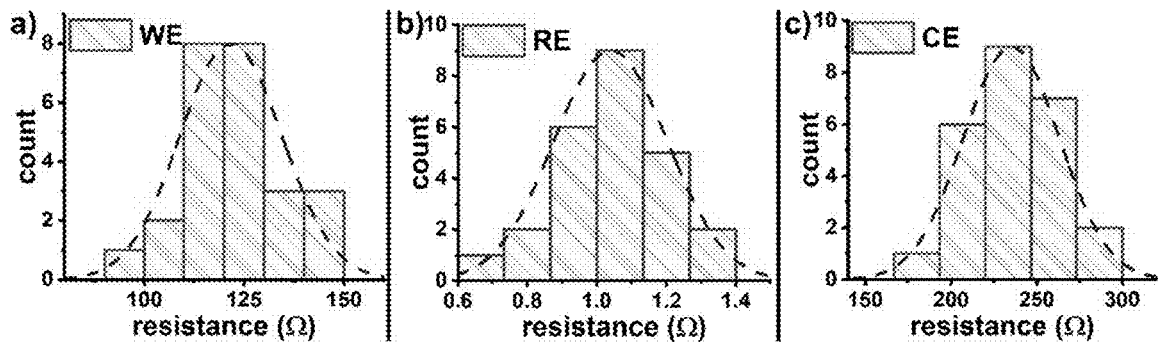
FIG. 2: Reproducibility of stencil printed electrodes. The distribution of the measured resistances of (a) working electrode, (b) reference electrode, and (c) counter electrode used to measure UA with OPSBs.

Fabrication of Omniphobic Paper-Based Uric Acid (UA) Sensors to Monitor Open Chronic Wounds Whatman #1 paper was made omniphobic by spraying it with a 2% solution of fluorinated alkyltrichlorosilane ($R^F SiCl_3$) in iso-propyl alcohol (IPA) and drying it in a desiccator at 36 Torr for 20 min. See Glavan, A. C., Martinez, R. V., Maxwell, E. J., Subramaniam, A. B., Nunes, R. M. D., Soh, S., Whitesides, G. M., 2013. Rapid fabrication of pressure-driven open-channel microfluidic devices in omniphobic RF paper. Lab Chip 13, 2922. https://doi.org/10.1039/c31c50371b. Three flexible electrodes were stencil printed on the omniphobic paper using conductive inks: working (WE) and counter (CE) electrodes with carbon ink, reference electrode (RE) and contact pads with Ag/AgCl ink (FIG. 1). The conductive inks were dried in a desiccator at 36 Torr for 30 min, producing electrodes with highly reproducible conductivities (FIG. 2). Prior to mounting the paper-based UA sensors on the adhesive bandages, about 5 μL of a uricase solution was drop casted on the electrochemical test zone and allowed it to dry at room temperature. Uricase (from *Candida* sp.) was used as it has been shown to have excellent selectivity towards UA. The presence of potential interferants available in wound exudate—such as creatinine, glucose, lactate, or ascorbic acid—has also been demonstrated to have no significant effect on the selectivity of uricase. The uricase solution was prepared by mixing 3 μg/mL uricase with a 100 mM solution of potassium ferricyanide in 1:1 ratio. All solutions were made in phosphate buffered saline (PBS, 1×, pH 7.4). To calibrate the wearable potentiostat, different concentrations (0.2 to 1 mM in steps of 0.2 mM) of UA in PBS were used. About 5 μL of the uric acid solutions were pipetted over the uricase modified electrodes and performed chronoamperometric assays using a 300 mV step potential (with respect to the RE) at a sampling rate of 10 Hz. The use of such a low working potential ensures minimal interference from other easily oxidized species in the wound exudate. Integrating the measured current with respect to time enabled the calculation of the net charge exchanged during the redox reaction by chronocoulometry (Eq. S2).

Fabrication of Omniphobic Paper-Based pH Sensors to Monitor Open Chronic Wounds

Figure 3:
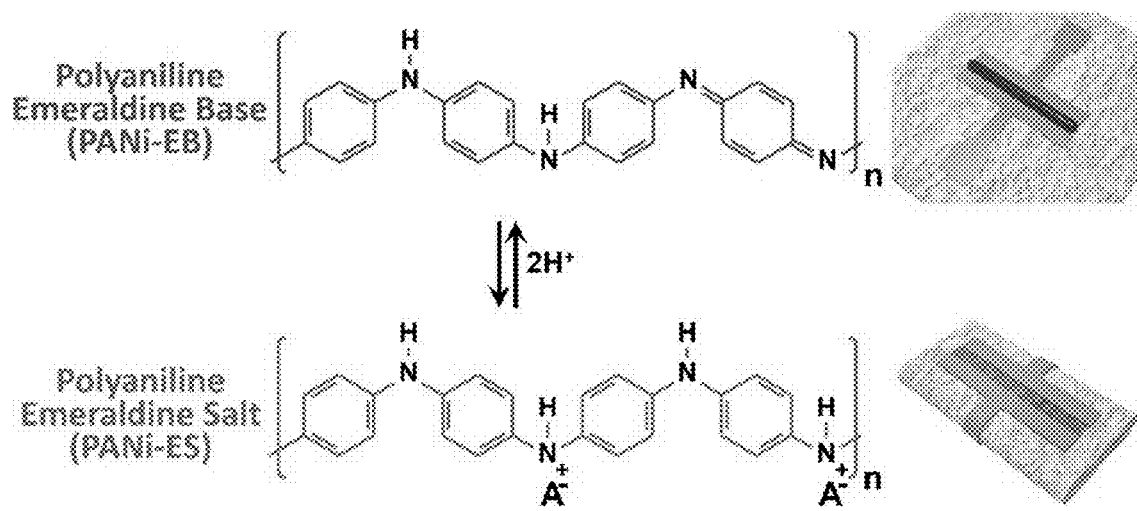
FIG. 3. Chemical structures of PANi-EB and PANi-ES and their reversible transformation by protonic acids.

Ag/AgCl ink was used to print the electrodes of the pH sensors. A pH-responsive polymeric composite was prepared by mixing 150 mg of PANi-EB with 250 mg of silver microflakes (particle size 2-5 μm, Inframat® Advanced Materials™ LLC) (FIG. 3) in 5 mL of IPA. The mixture was sonicated for 1 h to create a uniform suspension. About 10 μL of the Ag/PANi-EB solution was pipetted between the electrodes of the pH sensor and dried it at 60° C. for 30 mins to create a thin solid film of Ag/PANi-EB composite (blue colored). The Ag/PANi-EB composite was exposed to hydrochloric acid (HCl) vapors in a desiccator at 36 Torr for 30 min. The $H^+$ ions from the HCl vapors transform the PANi-EB part of the composite into its emeraldine salt (ES) form (green colored), which exhibits a higher conductivity (FIG. 3). The Ag/PANi-ES pH sensors were rinsed with deionized water and dried them in a nitrogen stream before their embedding into a commercial bandage.

The pH buffer solutions (McIlvaine) across the clinical range of open wound exudate (5.5-8.5) was prepared to calibrate the pH sensors. McIlvaine buffers were prepared by mixing 0.2 M solution of disodium phosphate and a 0.1 M solution of citric acid in different ratios (Table 1). The pH of all the resulting solutions was verified using a digital pH meter (Model IQ125, IQ Scientific Instruments, USA). About 10 μL of the pH buffers were pipetted on the Ag/PANi-ES composite and performed impedance spectroscopy across the electrodes by applying sinusoidal signals with an amplitude of 100 mV and frequencies ranging 10 Hz-100 kHz to calibrate the measured impedance with pH.

TABLE 1

McIlavine buffer compositions used to generate the 20-mL-solutions with pH values ranging 5.5 to 8.5

| pH | 0.2 M disodium phosphate (mL) | 0.1 M citric acid (mL) |
|---|---|---|
| 5.5 | 11.5 | 8.5 |
| 6.0 | 12.6 | 7.4 |
| 6.5 | 14.5 | 5.5 |
| 7.0 | 16.5 | 3.5 |
| 7.5 | 18.0 | 2.0 |
| 8.0 | 19.5 | 0.5 |
| 8.5 | 20.0 | 0.0 |

Fabrication of Omniphobic Paper-Based Impedance Sensor Array to Monitor Pressure Ulcers Seven equidistant electrodes in a hexagonal array were printed using Ag/AgCl ink on omniphobic Whatman #1 paper to measure, in vivo, tissue impedance across pressure ulcers models induced on mice (FIG. 1). To improve the electrical contact between the electrodes and the skin of the mice, the electrodes were selectively coated with a conductive hydrogel (SPECTRA® 360, Parker Laboratories Inc.) using a stencil mask. The omniphobic paper substrate impeded the spreading of the conductive hydrogel over the paper, and avoided short circuits among the electrodes. After placing the electrode array on the shaved skin of the mouse and ensuring its uniform contact, impedance data was recorded from each pair of nearest neighbor electrodes. The wearable potentiostat enables the detection of tissue damage using a AD5933 impedance analyser chip and transmits the results to the user via an RF transceiver module. The AD5933 chip applied signals with an AC voltage of 0.97 V, DC bias of 0.76 V, and frequencies ranging 1 to 100 kHz to perform impedance spectroscopy. The wearable potentiostat reads the response signal, and calculates the magnitude and phase of the impedance of the underlying tissue.

Early In Vivo Detection of Pressure Ulcers

Figure 4:
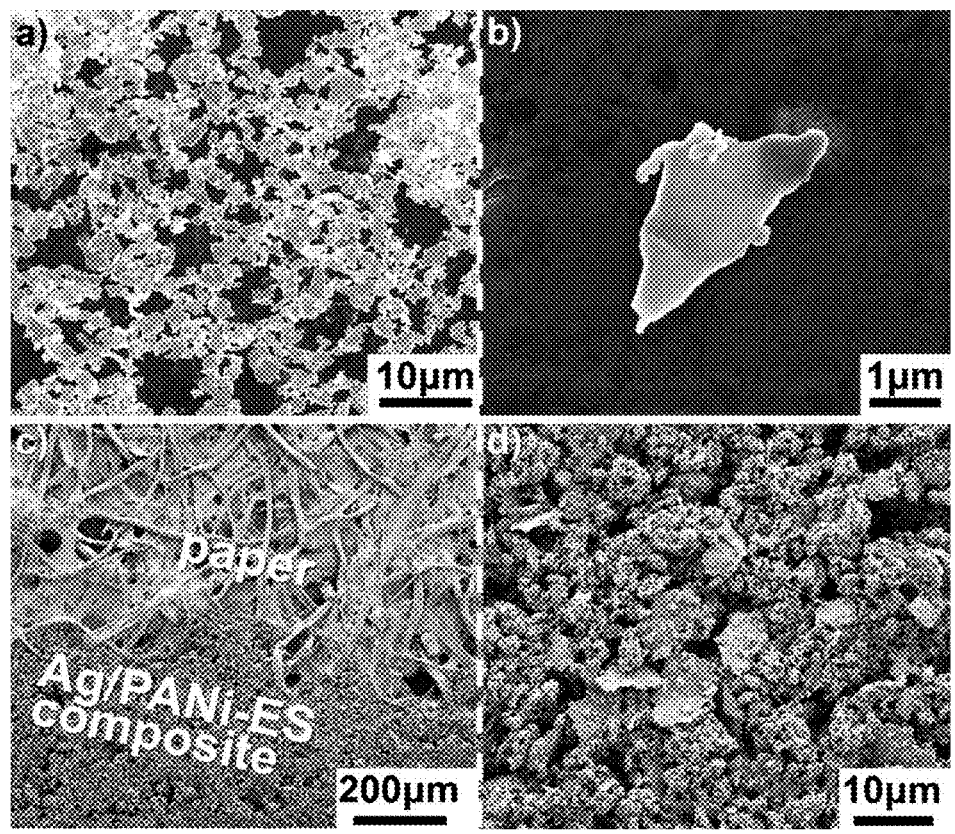
FIG. 4. Scanning electron microscopy images of Ag/PANi layers. (a) Ag microflakes used to increase the conductivity of PANi-EB. (b) High resolution SEM image of a representative microflake. (c) Image of Ag/PANi-ES layer printed on Whatman #1 paper. (d) High resolution SEM image of the Ag/PANi-ES composite.

Ten laboratory mice (C57B6J, 8-15 weeks old, male) with mixed backgrounds were used to detect pressure-induced tissue damage in vivo. A ketamine-xylazine cocktail (0.1 g per kg of body weight). was used to anaesthetize the mice. Two disc magnets (D601, www.kjmagnetics.com; NdFeB, 10 mm diameter, 2 mm thickness) were used to controllably create a pressure ulcer model on mice. Prior to the application of the magnets, hair was removed from the back of the mice using depilatory cream (Nair) and then the area was washed with mild detergent (Dawn). The shaved skin of the mice was gently tented up and placed between the two disc magnets (FIG. 4), which applied a ~6.7 kPa pressure during the ischaemia cycle. The magnets did not interfere with the normal activity of the mice after they recovered from the anesthesia. The magnets were kept in place for 1 or 3 h to create different degrees of tissue damage. Each mouse received only one pressure-induced wound, and impedance measurements of the damaged tissue were collected for three days after the ischaemia cycle. During the measurements, the wearable potentiostat placed over the anesthetized mouse performed impedance spectroscopy across each pair of nearest neighbor electrodes in the array (FIG. 1). After sampling all the electrodes and transmitting the results wirelessly to a laptop, a map of the impedance of the tissue was constructed and used to assess the healing process of tissue damaged by 1 h- and 3 h-long ischaemic events. Registration marks were drawn onto the skin of the mice to locate the different features of the pressure ulcer with respect to the position of the electrodes. The same OPSB was used to collect impedance measurements, once per day, over three consecutive days. All procedures involving mice were performed in accordance with Purdue University's Animal Care and Use Committee.

Results and Discussion

Design and Assembly of OPSBs

Figure 5:
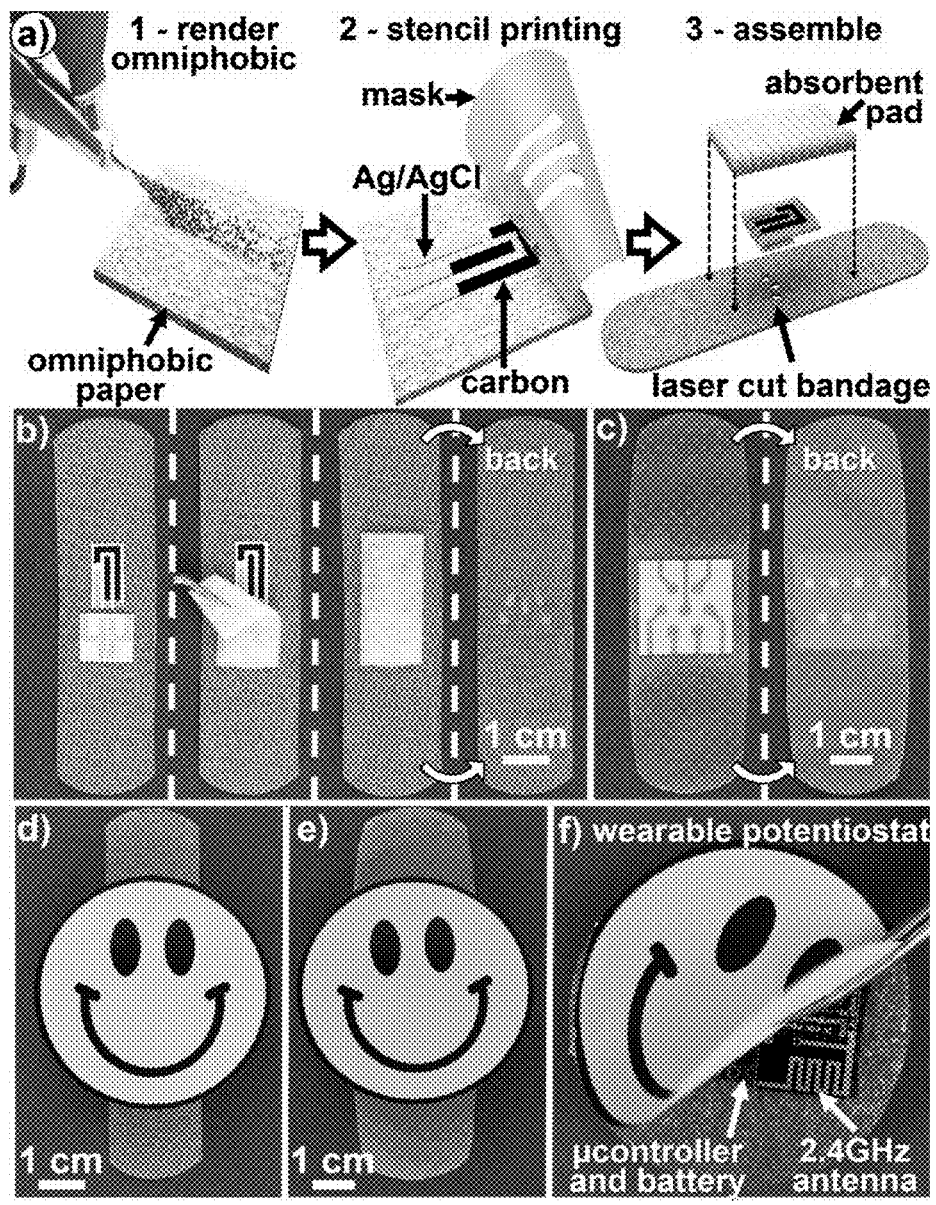
FIG. 5. OPSB fabrication and assembly process. (a) Schematic diagram of the fabrication of OPSBs: 1) Whatman #1 paper is rendered omniphobic by spraying a 2% solution of $R^FSiCl_3$ in IPA; 2) stencil printing is used to pattern flexible conductive electrodes using carbon and Ag/AgCl inks; 3) openings are laser cut on the adhesive layer of the bandage to interface the wearable potentiostat with the paper-based sensors in the OPSB. OPSBs are assembled by placing the paper-based sensors between the adhesive layer and the absorbent pad of the commercial bandages. (b) OPSBs used to monitor uric acid and pH levels in open wounds. (c) OPSBs used for the early detection of pressure ulcers. (d, e) Interfacing of the wearable potentiostat with OSPBs for monitoring open wounds and detecting pressure ulcers, respectively. (f) Packaging of the electronics in the rechargeable, wearable potentiostat.
Figure 6:
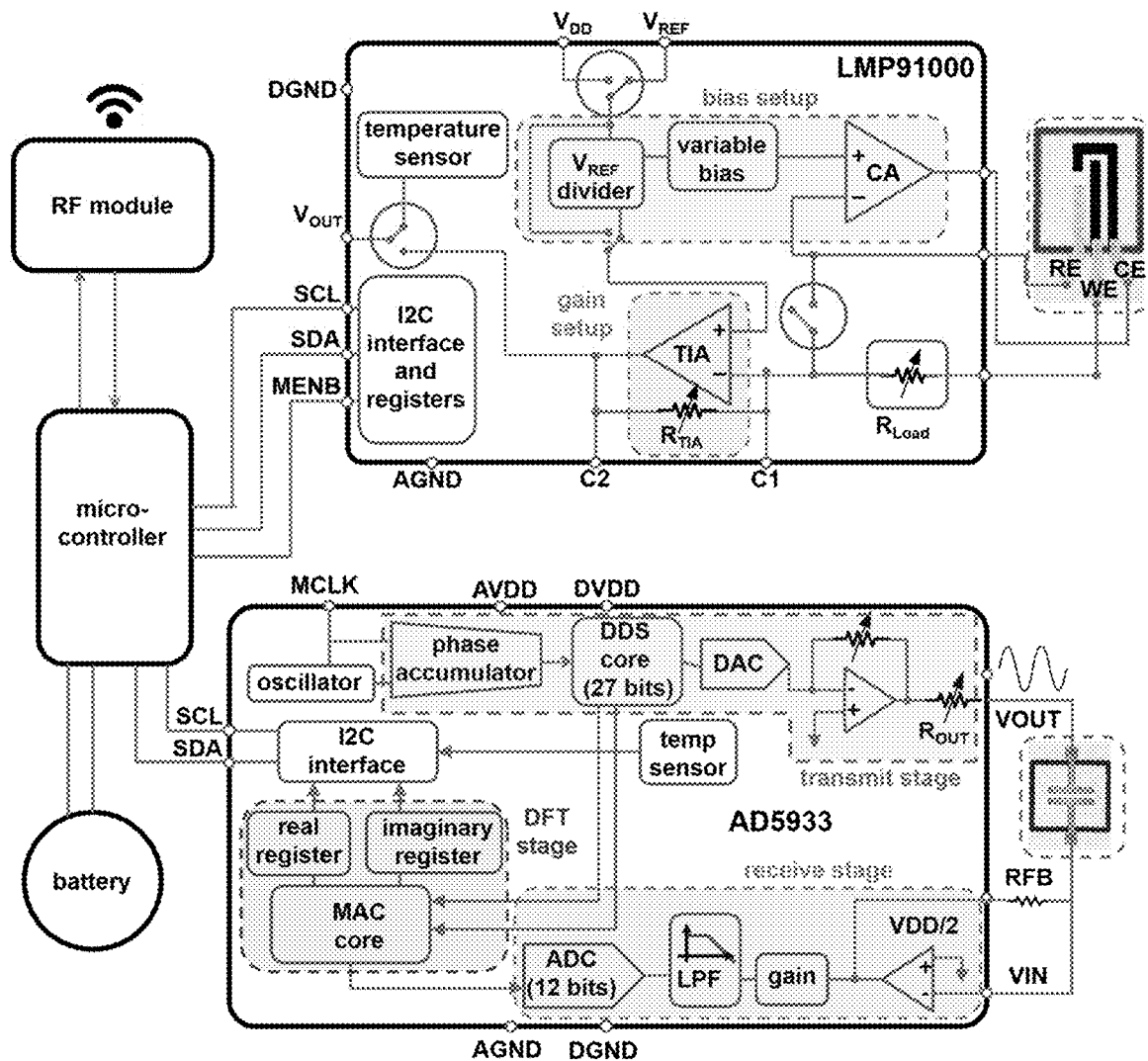
FIG. 6: Schematics of the electronics in the wearable potentiostat used for wireless chronic wound monitoring. The LMP91000 and AD5933 chips performed electrochemical measurements and impedance spectroscopy, respectively. Both chips are controlled by a microcontroller and powered by a rechargeable 3.6 V battery. Test results are wirelessly transmitted by a radio frequency communication module.

FIG. 5a depicts the fabrication steps followed to make OPSBs. Flexible electrodes were fabricated by screen printing conductive inks on paper, which was previously rendered omniphobic by spraying a solution of $R^FSiCl_3$ in IPA. The silane, while chemically modifying the cellulose fibers, does not block the pores of the paper, preserving its breathability to ensure oxygenation of the wound. These paper-based sensors are then embedded into commercial bandages to create the OPSBs (FIG. 5a-5c), without compromising the flexibility of the bandage. Laser cut openings on the adhesive bandage and folded the contact pads of the sensors to allow them to interface with the wearable potentiostat (FIG. 5a). The absorbent pad of the bandage transfers the wound exudate to the surface of the paper-based sensors. Two sets of OPSBs were fabricated: one with sensors capable of monitoring both UA and pH levels in the exudate of open wounds (FIG. 5b), another with an electrode array capable of detecting pressure ulcers (FIG. 5c). After the bandage is applied on top of the wound, a single-use, double-sided adhesive layer sticks the wearable potentiostat to the OPSB, making it easy to apply, and securing the electric contacts with the paper-based sensors. To change these smart dressings, simply remove the OPSB (while still attached to the wearable potentiostat) from the skin of the user and then peel the wearable potentiostat from the adhesive layer Characterization of the Wearable Wireless Potentiostat A lightweight (~8 g) and low-cost (~$18) wearable potentiostat was developed. The potentiostat is capable of performing 3-electrode electrochemical measurements and impedance spectroscopy (FIG. 6). The housing of the potentiostat was designed as a "smiley face" to promote patient adoption of the device (FIG. 5d-5f). The wireless communication module integrated in the wearable potentiostat transmits the measurements so that the results can be stored and displayed on the user's phone or laptop and then transferred from on-site to experts, over the web, to facilitate remote consultation. Additionally, the wireless card in the wearable potentiostat enables the wireless reconfiguration of the LMP91000 and the AD5933 chips through the microcontroller, making it possible to choose between impedance spectroscopy, chronoamperometry, and chronocoulometry, as well as to select the proper scanning parameters, for a fully automated wireless monitoring of wound status. A 3.6 V rechargeable battery powers the microcontroller and the low-power chemical sensors using low supply currents (<15 µA), maximizing battery life (over 7 days, measuring once every two hours) and making the device safe for the patient. While OPSBs can be easily disposed by incineration, the wearable potentiostat can be reused, after its sterilization and recharging by attaching it to a new OPSB.

Figure 7:
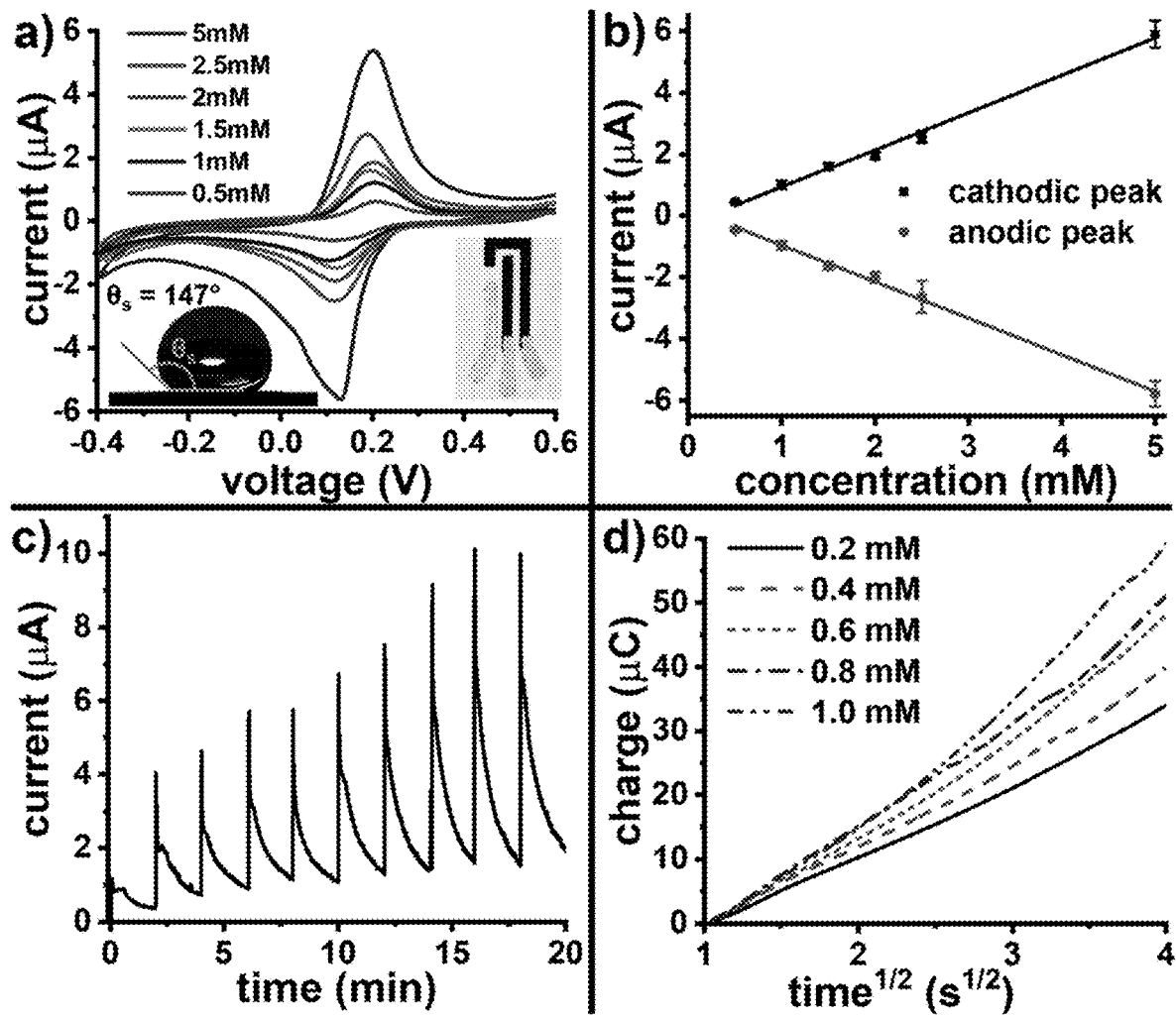
FIG. 7: Characterization of the electrochemical performance of the flexible electrodes stencil-printed on omniphobic paper substrates. (a) Cyclic voltammograms recorded with the wearable potentiostat for various concentrations of potassium ferricyanide in PBS at a scan rate of 10 mV/s. The insets show the static contact angle (147°) of water on omniphobic Whatman #1 paper and the electrodes used. (b) Dependence of the anodic and the cathodic peak currents on the concentration of potassium ferricyanide (average RSD=8% and 12% respectively). (c) Chronoamperometric current response measured by applying a constant potential of 300 mV with respect to the RE, as increasing concentrations of potassium ferricyanide in PBS (0.1-1 mM, in steps of 0.1 mM) are added at 2 min intervals. (d) Linear dependence of the exchanged charge on the square root of time for the different concentrations of potassium ferricyanide, as expected from the Cottrell equation (Eq. 51).

To characterize the electrochemical performance of the OPSB s and the wearable potentiostat, cyclic voltammetry (CV) was performed with several solutions of ferricyanide/ferrocyanide, one of the electroactive systems most commonly used for testing electrochemical electrodes. FIG. 7a shows the voltammograms of several concentrations (0.5, 1.0, 1.5, 2.0, 2.5, and 5.0 mM) of potassium ferricyanide in PBS, recorded with the wearable potentiostat while applying a linear voltage sweep from –0.4 V to 0.6 V at 10 mV/s scan rate. The linear relationship between the anodic and cathodic peak currents and the square root of the scan rates ($R^2$=0.993 and 0.997 respectively. FIG. 7b demonstrates that the OPSBs and the wearable potentiostat are suitable to perform electrochemical analysis. FIG. 7c shows the chronoamperometric current response for gradually increasing potassium ferricyanide concentrations. The linear relationship between the net exchanged charge and the square root of time (FIG. 7d) verifies that the reaction is diffusion controlled and governed by the Cottrell equation (Eq. S1).

Real-Time Monitoring of Uric Acid Using OPSBs

Figure 8:
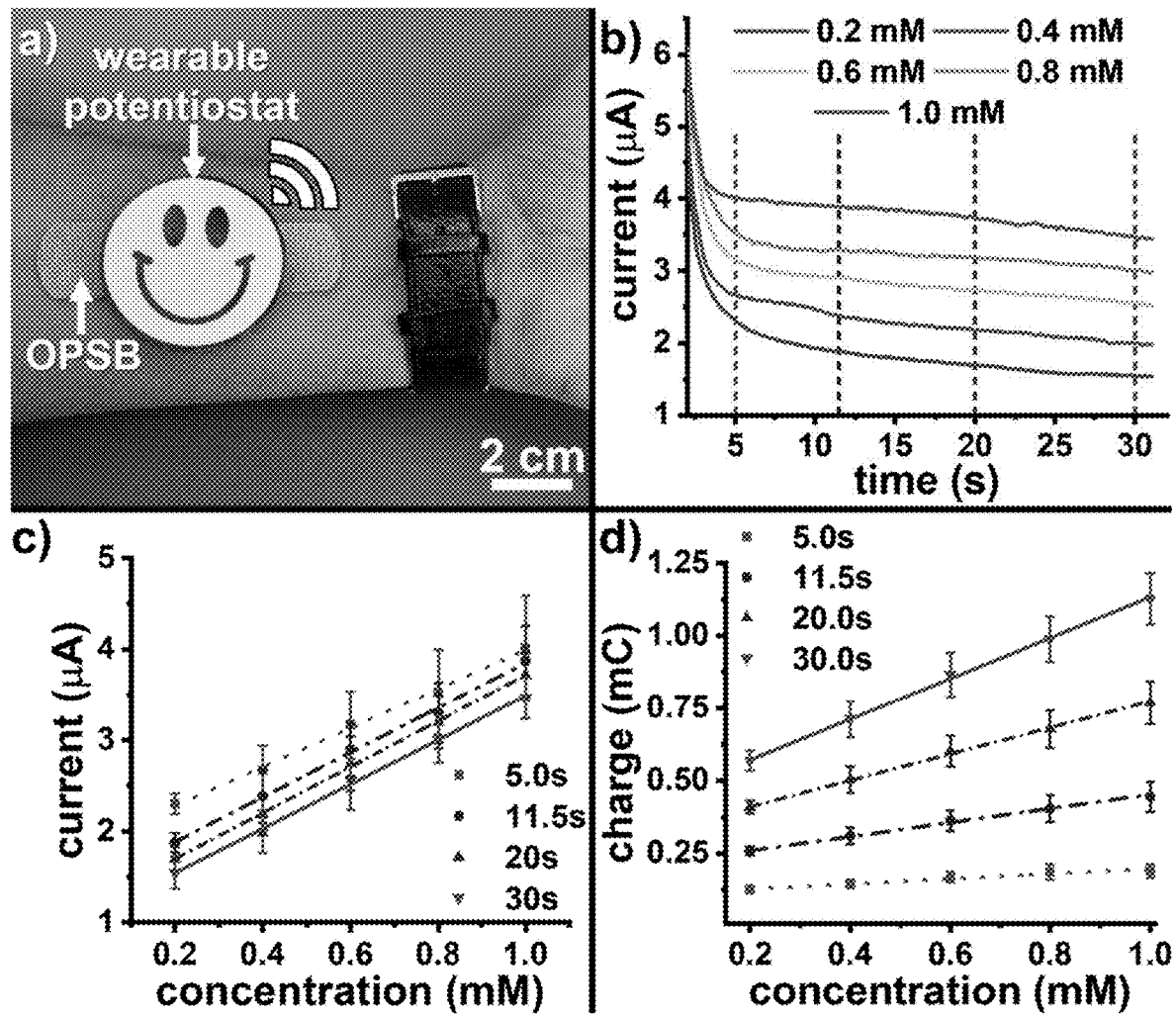
FIG. 8: Real-time monitoring of UA using OPSBs and a wearable potentiostat. (a) Picture of the wearable potentiostat interfacing a functional OPSB. The wearable potentiostat can be easily adhered on top of the smart bandage and removed, sterilized, and reused on different bandages. (b) Chronoamperograms measured with the wearable potentiostat for different concentrations of UA in the wound model. (c) Calibration plots of the current as a function of the concentration of UA at different reading times: 5 s ($\overline{R}^2$=0.996, average RSD=10.8%), 11.5 s ($\overline{R}^2$=0.997, average RSD=9.6%), 20 s ($\overline{R}^2$=0.998, average RSD=8.9%), and 30 s ($\overline{R}^2$=0.998, average RSD=10.1%). (d) Linear dependence of the total charge measured by chronocoulometry on the concentration of UA at different reading times: 5 s ($\overline{R}^2$=0.957), 11.5 s ($\overline{R}^2$=0.995), 20 s ($\overline{R}^2$=0.998), and 30 s ($\overline{R}^2$=0.999).

The electrochemical measurement of UA levels in open wounds can be used to monitor bacterial infection. A method of this disclosure used the OPSBs and the wearable potentiostat to wirelessly measure different concentrations of UA in a wound exudate model (FIG. 8). The UA is oxidized to allantoin by the uricase in the OPSB, while potassium ferricyanide is reduced to potassium ferrocyanide (Eq. S3). Using chronoamperometry, the linear relationship between the oxidation current and the concentration of UA (FIG. 8b, 8c) can be calibrated, according to the Cottrell equation (Eq. S1). FIG. 8d shows the performance of the wearable potentiostat and the OPSBs to acquire and wirelessly transmit chronocoulometry measurements of UA. We noticed that using chronocoulometry provides more reliable quantitative measurements of the concentration of UA when compared to chronoamperometry, as any random experimental noise is averaged out by integrating the oxidation current over time (Eq. S2). OPSBs, calibrated using the curve shown in FIG. 8d, exhibit a limit of detection for UA of 0.2 mM using the wearable potentiostat in chronocoulometry configuration, demonstrating the accurate sensing of these smart bandages over the clinically relevant range for open chronic wounds (0.22-0.75 mM).

Determination of pH Levels Using OPSBs

Figure 9:
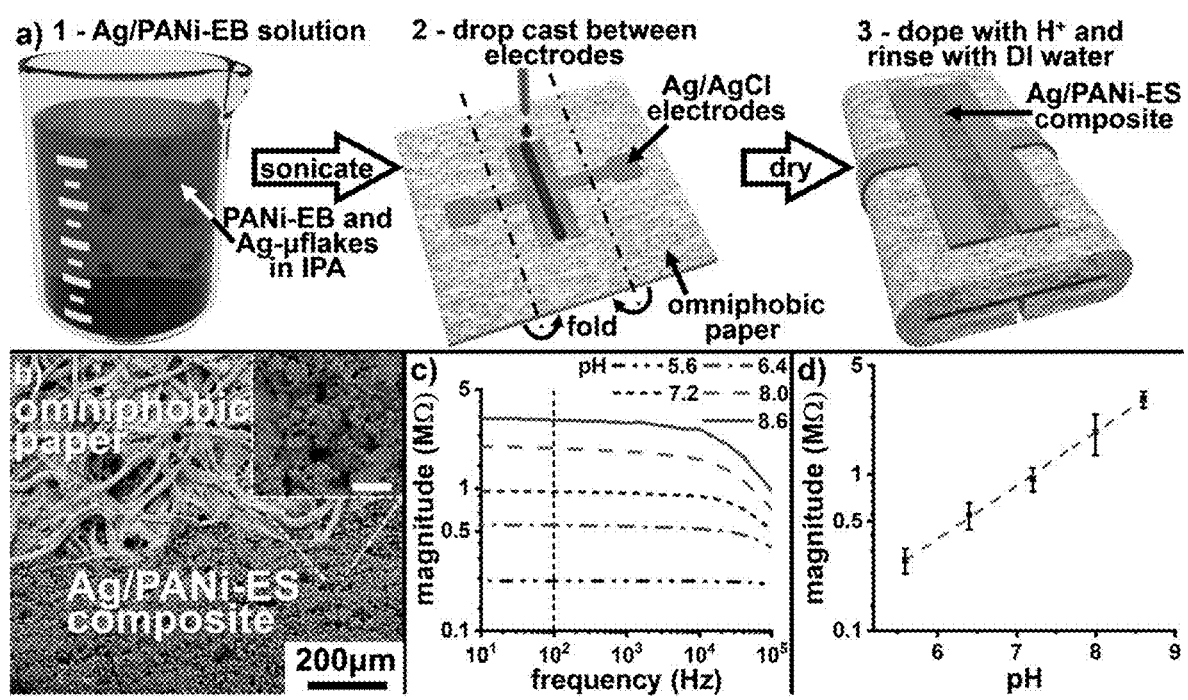
FIG. 9: Monitoring pH with OPSBs with Ag/PANi composite electrodes. (a) Schematic diagram describing the fabrication of the pH sensors: (1) PANi-EB is added to a suspension of silver microflakes in IPA and sonicated. (2) The resulting solution is drop cast between the stencil-printed electrodes and dried to create an Ag/PANi-EB layer. (3) The Ag/PANi-EB composite is doped with H+ ions from HCl vapors, converting the PANi-EB to PANi-ES. (b) SEM image of a Ag/PANi-ES composite layer on omniphobic paper. The inset shows a high-resolution, false-colored SEM image of the Ag/PANi-ES composite with PANi-ES in green and Ag microflakes in blue (scale bar is 10 µm). (c) Bode diagram of the magnitude of the impedance for wound exudate models with different pH values. (d) Calibration of magnitude of the impedance, measured at 100 Hz, as a function of the pH ($\overline{R}^2$=0.998).

The wearable potentiostat can also be wirelessly configured to operate as a resistive sensor to accurately quantify pH levels of a wound exudate model (FIG. 9). To measure pH, the method of this disclosure used OPSBs with a pair of Ag/AgCl parallel electrodes printed on omniphobic paper and separated by a layer of Ag/PANi-ES composite (FIG. 9a, 9b). PANi-ES gradually transforms into PANi-EB (more resistive) when exposed to alkaline pH environments. Silver microflakes decrease the resistivity of PANi, facilitating the accurate determination of the pH of the wound exudate by applying low voltages (100 mV). The impedance across the electrodes of the pH sensor was measured over frequencies ranging 10 Hz-100 kHz and it was observed no frequency dependence of the impedance up to 10 kHz (FIG. 5c). A frequency of 100 Hz was chosen to calibrate the relationship between pH and impedance for our omniphobic, paper-based sensors (FIG. 9d). The PANi in the OPSB undergoes a reversible chemical transformation between PANi ES and PANi EB (FIG. 3) depending on the concentration of $H^+$ ions of its surroundings. The impedance measured by the pH sensor correlates linearly with the concentration of $H^+$ (and thus exponentially with the pH) in the wound exudate model. After the OPSBs and the wearable potentiostat are calibrated using the curve shown in FIG. 9d, they can be used to accurately quantify pH levels across the clinically relevant pH range for open chronic wounds (5.5-8.5).

Early In-Vivo Detection and Monitoring of Pressure Ulcers Using OPSBs

Figure 10:
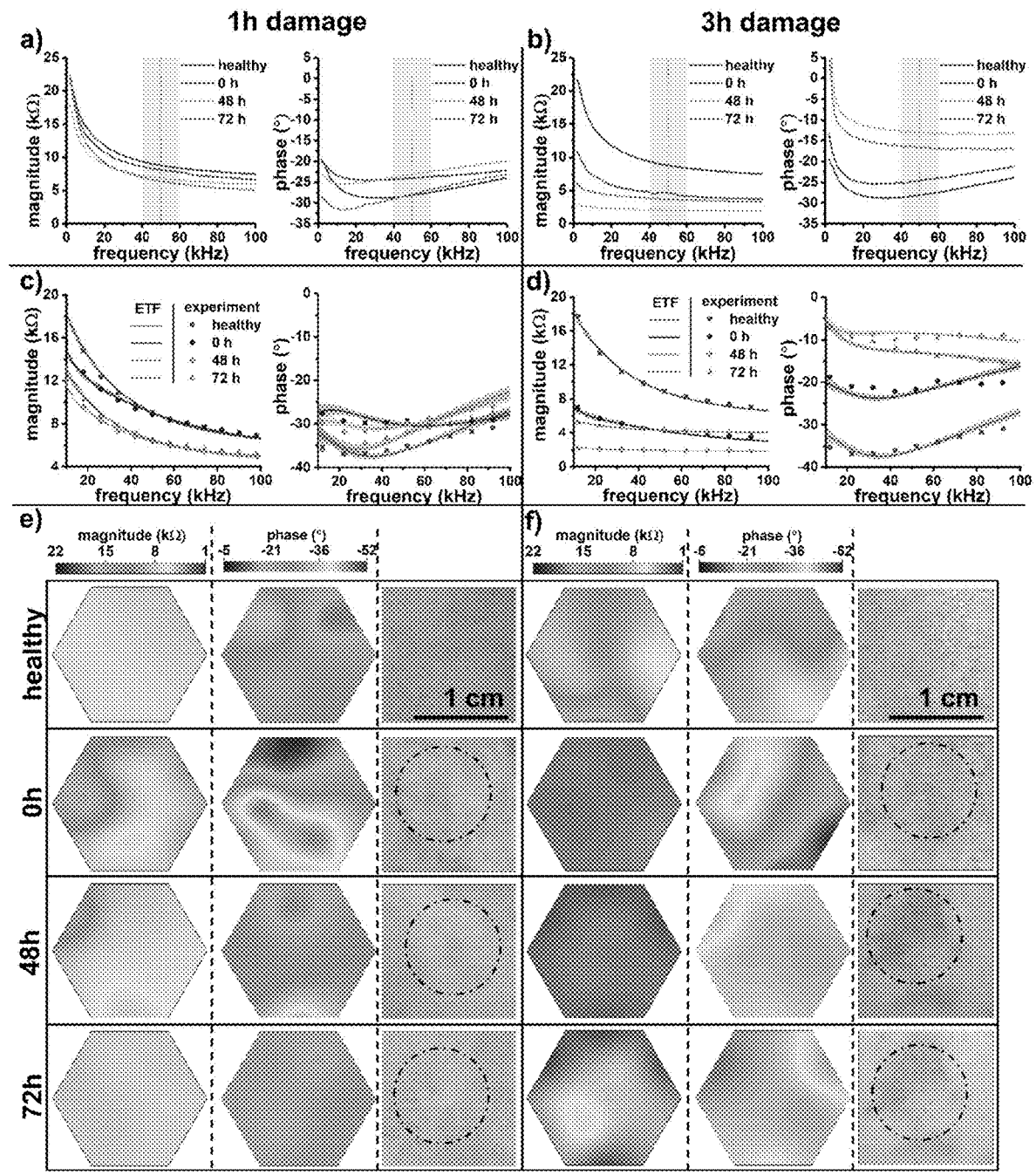
FIG. 10: Early in-vivo detection and monitoring of pressure-induced tissue damage using OPSBs. (a, b) Bode diagrams of the magnitude and phase of the impedance measured across pressure ulcers models induced on a mouse by 1 h (a) and 3 h (b) ischaemia cycles. "Healthy" indicates the control measurements taken before applying pressure to the tissue with two magnets. "0 h" corresponds to measurements taken immediately after the ischaemia cycle. "48 h" and "72 h" corresponds to measurements taken two and three days after the ischaemia cycle, respectively. (c, d) Dependence on frequency of the magnitude and phase of the impedance obtained from a representative pair of electrodes after 1 h (c) and 3 h (d) ischaemia cycles. The markers denote the experimentally measured data, while the solid lines and shaded regions show the ETF and the 95% fit confidence interval respectively. (e, f) Surface maps of the magnitude and phase of the impedance measured across the tissue damaged by 1 h (e) and 3 h (f) ischaemia cycles. Images of the damaged region are provided at the right of each map. The dashed circle corresponds to the size of the magnets and indicates where the pressure was applied.

While open chronic wounds are relatively simple to identify and monitor by analyzing wound exudate, the early identification of the formation of subcutaneous (closed) wounds is challenging because by the time the wound becomes visible on the skin, the tissue damage underneath is often already severe. FIG. 10 shows the early in-vivo detection and monitoring of pressure ulcers on a mouse model using OPSBs. Cell damage or death causes the breakage of the cellular membrane, allowing the ion-rich cytoplasm of the cell to merge with the extracellular fluid. This makes the damaged tissue more conductive and less capacitive compared to healthy tissue. FIG. 10a, 10b show that a 3 h ischaemic event decreases the magnitude of the impedance of the damaged tissue more than a 1 h event, according to the amount of damage induced to the tissue. Similarly, the phase of the impedance increases with the amount of damage caused by the ischaemic event. FIG. 10c, 10d show the estimated transfer functions (ETF) used to mathematically describe the impedance behavior of the in vivo model as a function of frequency. It was found that OPSBs provided a maximum contrast between the impedances of the healthy and damaged tissue over the 40-60 kHz frequency range. A central frequency of 50 kHz was chosen to create surface maps of impedance to detect damaged tissue under the bandage (FIG. 10e, 10f). The combination of magnitude and phase data makes the detection of pressure ulcers more reliable than detection methods using only one parameter. Using both magnitude and phase also minimizes the effect of experimental noise and random variations in animal characteristics (age, skin roughness, weight, etc.). 1 h ischaemic events cause an immediate damage of the underlying tissue that is partially recovered after 48 h and totally restored after 72 h (FIG. 10e). 3 h ischaemic events cause a damage of the underlying tissue that cannot complete its healing even after 72 h (FIG. 10f). These impedance maps demonstrate that the OPSBs and the wearable potentiostat can be used to non-invasively detect pressure-induced tissue damage, even when such damage cannot be visually identified (FIG. 10e, 10f). These results demonstrate the feasibility of using impedance measurements obtained with paper-based wireless smart bandages to detect pressure-induced tissue damage at an early stage and to monitor its healing process across multiple animals.

This disclosure provides a simple, low-cost, and non-invasive strategy to monitor open wound status wirelessly, using OPSBs. This disclosure also provides the demonstration of in-vivo early detection and monitoring of pressure ulcers using wireless smart bandages. OPSBs have five significant advantages over previously reported smart bandages: (i) They are lightweight, inexpensive to manufacture, easy to apply, and disposable by burning; (ii) a single OPSB can simultaneously quantify pH and UA at the wound site; (iii) they enable the early detection of pressure ulcers by providing a surface map of the location and severity of the tissue damage; (iv) the use of omniphobic paper as a flexible substrate facilitates oxygenation of the wound by preserving the gas permeability of the bandage, and enables accurate wound monitoring for up to three days without significant change in performance. Replacing OPSBs enables wound monitoring over longer periods of time; (v) the wearable potentiostat wirelessly reports quantitative information about the status of the wound, which can be used to inform the patient and remote medical staff about the need to change the bandage, disinfect the wound, or apply preventive treatment. The OPSB s and the wearable potentiostat described here, at their present level of development, also have two limitations: (i) The accuracy of the measurements on open wounds performed with Ag/AgCl reference electrodes depends on the chloride concentration, which, while it is expected to be tightly regulated within the blood, might vary over the injury depending on the wound dynamics; (ii) to measure the in-vivo impedance of pressure ulcers, OPSBs use a two-point probe configuration, rather than the theoretically more accurate, four-point probe configuration. This approach is taken due to the lack of homogeneity in the impedance of the skin and the non-ideal connections between the electrodes and the user; an inherent complication while measuring impedance on complex biological tissues. The strategy to integrate omniphobic paper-based sensors in commercially available dressings is, however, versatile, applicable to other biosensors and, with further development, will be able to expand the sensing repertoire of current smart bandages to monitor the healing process of chronic wounds.

Those skilled in the art will recognize that numerous modifications can be made to the specific implementations described above. The implementations should not be limited to the particular limitations described. Other implementations may be possible.

Arduino Code to Operate the Wearable Potentiostat

Arduino Code to Perform Chronoamperometry Using the LMP91000 Chip

```
#include <Wire.h>
#include "LMP91000.h"
int NumberOfScans = 1;
int Amp350Time = 10; //in minutes
int Amp120Time = 4; //in minutes
int Amp35Time = 6; //in minutes
int InitialDelayTime = 10; //in milliseconds
int ScanNumber = 0;
LMP91000 lmp91000;
int NoOf350Samples = Amp350Time * 600; // 10 readings per second
int NoOf120Samples = Amp120Time * 600; // 10 readings per second
int NoOf35Samples = Amp35Time * 600; // 10 readings per second
void setup(void) {
   Serial.begin(115200);
   Serial.println("LMP91000 Test");
   Serial.println(NoOf120Samples);
   Serial.println(NoOf350Samples);
   Wire.begin( );
}
void loop (void){
   lmp91000.configure(
```

```
    LMP91000_TIA_GAIN_350K     | LMP91000_RLOAD_10OHM,
    LMP91000_REF_SOURCE_INT | LMP91000_INT_Z_20PCT |
    LMP91000_BIAS_SIGN_POS | LMP91000_BIAS_0PCT,
    LMP91000_FET_SHORT_DISABLED | LMP91000_OP_MODE_AMPEROMETRIC
  );
  if (millis( ) > InitialDelayTime) {
    if (ScanNumber < NumberOfScans) {
      lmp91000.configure(
        LMP91000_TIA_GAIN_350K      | LMP91000_RLOAD_10OHM,
        LMP91000_REF_SOURCE_INT | LMP91000_INT_Z_20PCT |
        LMP91000_BIAS_SIGN_POS | LMP91000_BIAS_6PCT,
        LMP91000_FET_SHORT_DISABLED | LMP91000_OP_MODE_AMPEROMETRIC
      );
      Serial.print("Config Result: ");
      Serial.println(res);
      for (int i = 0; i < NoOf350Samples; i++) {
        delay (100);
        Serial.println(analogRead(A1));
      }
      lmp91000.configure(
        LMP91000_TIA_GAIN_120K      | LMP91000_RLOAD_10OHM,
        LMP91000_REF_SOURCE_INT | LMP91000_INT_Z_20PCT |
        LMP91000_BIAS_SIGN_POS |LMP91000_BIAS_6PCT,
        LMP91000_FET_SHORT_DISABLED | LMP91000_OP_MODE_AMPEROMETRIC
      );
      Serial.print("Config Result: ");
      Serial.println(res);
      for (int i = 0; i < NoOf120Samples; i++){
        delay (100);
        Serial.println(analogRead(A1));
      }
      lmp91000.configure(
        LMP91000_TIA_GAIN_35K       | LMP91000_RLOAD_10OHM,
        LMP91000_REF_SOURCE_INT | LMP91000_INT_Z_20PCT |
        LMP91000_BIAS_SIGN_POS | LMP91000_BIAS_6PCT,
        LMP91000_FET_SHORT_DISABLED | LMP91000_OP_MODE_AMPEROMETRIC
      );
      Serial.print("Config Result: ");
      Serial.println(res);
      for (int i = 0; i < NoOf35Samples; i++){
        delay (100);
        Serial.println(analogRead(A1));
      }
      ScanNumber = ScanNumber +1;
      Serial.print("Scan ");
      Serial.print(ScanNumber);
      Serial.print(" Complete");
    }
  }
}
```

Arduino Code to Perform Impedance Spectroscopy Using the AD5933 Chip

```
#include "Wire.h"
#define button 2
#define SLAVE_ADDR 0x0D
#define ADDR_PTR 0xB0
#define START_FREQ_R1 0x82
#define START_FREQ_R2 0x83
#define START_FREQ_R3 0x84
#define FREG_INCRE_R1 0x85
#define FREG_INCRE_R2 0x86
#define FREG_INCRE_R3 0x87
#define NUM_INCRE_R1 0x88
#define NUM_INCRE_R2 0x89
#define NUM_SCYCLES_R1 0x8A
#define NUM_SCYCLES_R2 0x8B
#define RE_DATA_R1 0x94
#define RE_DATA_R2 0x95
#define IMG_DATA_R1 0x96
#define IMG_DATA_R2 0x97
#define TEMP_R1 0x92
#define TEMP_R2 0x93
#define CTRL_REG 0x80
#define CTRL_REG2 0x81
#define STATUS_REG 0x8F
const float MCLK = 16.776 * pow(10, 6); // AD5933 Internal Clock Speed 16.776 MHz
const float start_freq = 60 * pow(10, 3); // Set start_freq, < 100Khz
const float incre_freq = 1 * pow(10, 3); // Set freq increment
const int incre num = 40; // Set number of increments; < 511
char state;
void setup( ) {
  Wire.begin( );
  Serial.begin(115200);
  pinMode(button, INPUT);
  writeData(CTRL_REG, 0x0);      //clear ctrl-reg
  writeData(CTRL_REG2, 0x10);    //reset ctrl register
  programReg( );
}
void loop( ) {
  if (Serial.available( ) > 0) {
    state = Serial.read( );
    switch (state) {
      case 'A':   //Program Registers
        programReg( );
        break;
```

```
      case 'B':   //Measure Temperature
        measureTemperature( );
        break;
      case 'C':
        runSweep( );
        delay (1000);
        break;
    }
    Serial.flush( );
  }
}
void programReg( ) {
  writeData(CTRL_REG, 0x01);          // Set Range 1, PGA gain 1
  writeData(NUM_SCYCLES_R1, 0x07);       // Set settling cycles
  writeData(NUM_SCYCLES_R2, 0xFF);
  // Start_frequency of 1kHz
  writeData(START_FREQ_R1, getFrequency(start_freq, 1));
  writeData(START_FREQ_R2, getFrequency(start_freq, 2));
  writeData(START_FREQ_R3, getFrequency(start_freq, 3));
  // Increment by 1 kH
  writeData(FREG_INCRE_R1, getFrequency(incre_freq, 1));
  writeData(FREG_INCRE_R2, getFrequency(incre_freq, 2));
  writeData(FREG_INCRE_R3, getFrequency(incre_freq, 3));
  // Points in frequency sweep (100), max 511
  writeData(NUM_INCRE_R1, (incre_num & 0x001F00) >> 0x08 );
  writeData(NUM_INCRE_R2, (incre_num & 0x0000FF));
}
void runSweep( ) {
  short re;
  short img;
  double freq;
  double mag;
  double phase;
  double gain;
  double Impedance;
  double GF;
  double FFW;
  double wt;
  double BF;
  double totmag = 0;
  double count = 0;
  double avgmag;
  double totimp = 0;
  double avgimp;
  int i = 0;
  double Resistance;
  double Reactance;
  programReg( );
  // 1. Standby '10110000' Mask D8-10 of avoid tampering with gains
  writeData(CTRL_REG, (readData(CTRL_REG) & 0x07) | 0xB0);
  // 2. Initialize sweep
  writeData(CTRL_REG, (readData(CTRL_REG) & 0x07) | 0x10);
  // 3. Start sweep
  writeData(CTRL_REG, (readData(CTRL_REG) & 0x07) | 0x20);
  while ((readData(STATUS_REG) & 0x07) < 4 ) {
    delay(100); // delay between measurements
    int flag = readData(STATUS_REG) & 2;
    if (flag == 2) {
      byte R1 = readData(RE_DATA_R1);
      byte R2 = readData(RE_DATA_R2);
      re = (R1 << 8) | R2;
      R1 = readData(IMG_DATA_R1);
      R2 = readData(IMG_DATA_R2);
      img = (R1 << 8) | R2;
      freq = start_freq + i * incre_freq;
      mag = sqrt(pow(double(re), 2) + pow(double(img), 2));
      totmag = totmag + mag;
      //Gain factor calibration
      GF = 103.496 * (pow(10, -11)) + 811.151 * (pow(10, -18)) *
(freq - start_freq); //100kohm 40-100kHz
      Impedance = 1 / (GF * mag);
      totimp = totimp +Impedance;
      count = count +1;
      Resistance = 1 / (GF * re);
      Reactance = 1 / (GF * img);
      phase = atan(double(img) / double(re));
      phase = (180.0 / 3.1415926) * phase; //convert phase angle to
degrees
      //Phase Calibration
      System phase = 118;
      phase = phase - 118;
      Serial.print("Frequency: ");
      Serial.print(freq / 1000);
      Serial.print(",kHz;");
      Serial.print(" Magnitude: ");
      Serial.print(mag);
      Serial.print(" Impedance: ");
      Serial.print(Impedance / 1000);
      Serial.println(",kOhm;");
      //Increment frequency
      if ((readData(STATUS_REG) & 0x07) < 4 ) {
        writeData(CTR1_REG, (readData(CTR1_REG) & 0x07) | 0x30);
        i++;
      }
      avgmag = totmag / count;
      avgimp = totimp / count;
    }
  }
  Serial.print(" Avg Mag: ");
  Serial.print(avgmag);
  Serial.print(",");
  Serial.print(" Avg Impedance: ");
  Serial.print(avgimp / 1000);
  Serial.print(",kOhm;");
  writeData(CTR1_REG, (readData(CTR1_REG) & 0x07) | 0xA0);
//Power down; writeData(CTR1_REG,0xA0);
}
void writeData(int addr, int data) {
  Wire.beginTransmission(SLAVE_ADDR);
  Wire.write(addr);
  Wire.write(data);
  Wire.endTransmission( );
  delay (1)
}
int readData(int addr) {
  int data;
  Wire.beginTransmission(SLAVE_ADDR);
  Wire.write(ADDR_PTR);
  Wire.write(addr);
  Wire.endTransmission( );
  delay (1)
  Wire.requestFrom(SLAVE_ADDR, 1);
  if (Wire.available( ) +22= 1) {
    data = Wire.read( );
  }
  else {
    data = -1;
  }
  delay (1)
  return data;
}
boolean measureTemperature( ) {
  writeData(CTR1_REG, 0x90);
  delay(10);
  int flag = readData(STATUS_REG) & 1;     //Check status reg for temp measurement available
  if (flag == 1) {     // Temperature is available
    int temperatureData = readData(TEMP R1) << 8;
    temperatureData |= readData(TEMP R2);
    temperatureData &= 0x3FFF; // remove first two bits
    if (temperatureData & 0x2000 == 1) { // negative temperature
      temperatureData -= 0x4000;
    }
    double val = double(temperatureData) / 32;
    temperatureData /= 32;
    Serial.print("Temperature: ");
    Serial.print(val);
    Serial.println("C.");
    writeData(CTR1_REG, 0xA0);     // Power Down '10100000'
    return true;
  } else {
    return false;
  }
}
```

-continued

```
byte getFrequency(float freq, int n) {
  long val = long((freq / (MCLK / 4)) * pow(2, 27));
  byte code;
  switch (n) {
    case 1:
      code = (val & 0xFF0000) >> 0x10;
      break;
    case 2:
      code = (val & 0x00FF00) >> 0x08;
      break;
    case 3:
      code = (val & 0x0000FF);
      break;
    default:
      code = 0;
  }
  return code;
}
```

We claim:

1. A method of detecting a condition of a wound or a pressure ulcer in the skin of a subject by (i) attaching a device to the wound or area of the pressure ulcer, wherein the device comprises:

a bandage comprising a first surface configured to face healthy skin or wounded tissue, and a second surface on an opposite side of the first surface;

a detachable potentiostat, which is attached to the second surface of the bandage and includes an electrochemical sensing application chip and an impedance analyzer chip to detect the condition of the wound or the pressure ulcer;

a porous, chemically modified omniphobic pad comprising a first side configured to be attached to the first surface of the bandage, and a second side that is on an opposite side of the first side;

an absorbent pad, wherein the absorbent pad is deposed on the second side of the porous, chemically modified omniphobic pad;

a sensor deposed between the absorbent pad and the second side of the porous, chemically modified omniphobic pad, wherein the sensor comprises a working electrode, a counter electrode, and a reference electrode, wherein the electrodes are stencil-printed on the porous, chemically modified omniphobic pad; and, when the condition of the wound is to be detected, dropcasting a PANi-EB/Ag comprising a polyaniline-emeraldine base and silver microflakes composite film between the electrodes, wherein the silver in the PANi-EB/Ag composite film has a particle size of 2-5 µm, and when the condition of the pressure ulcer is to be detected, dropcasting a hydrogel between the electrodes;

wherein the detachable potentiostat is configured to be connected to the sensor through a plurality of pathways on the bandage to enable communications between the detachable potentiostat and the sensor; and (ii) when the condition of the wound is to be detected, measuring a pH of a wound exudate by impedance spectroscopy, and when the condition of the pressure ulcer is to be detected, measuring a magnitude and a phase of an impedance by surface mapping before the pressure ulcer is visible on a surface of the skin of the subject and correlating the magnitude and the phase of the impedance to a degree of tissue damage caused by the pressure ulcer; and iii) monitoring the condition of the wound or the pressure ulcer with a mobile device.

2. The method of claim 1, wherein the wound condition to be monitored comprises a bacterial infection.

3. The method of claim 1, wherein the porous omniphobic pad is chemically modified by treating the porous omniphobic pad with $RSiCl_3$ fluorinated alkyltrichlorosilane.

* * * * *